(12) United States Patent
Boothalingam et al.

(10) Patent No.: US 11,839,467 B2
(45) Date of Patent: Dec. 12, 2023

(54) SIMULTANEOUS ESTIMATION OF COCHLEAR AND EFFERENT ACTIVITY

(71) Applicant: Northwestern University, Evanston, IL (US)

(72) Inventors: Sriram Boothalingam, Evanston, IL (US); Sumitrajit Dhar, Evanston, IL (US)

(73) Assignee: Northwestern University, Evanston, IL (US)

( * ) Notice: Subject to any disclaimer, the term of this patent is extended or adjusted under 35 U.S.C. 154(b) by 1204 days.

(21) Appl. No.: 16/398,708

(22) Filed: Apr. 30, 2019

(65) Prior Publication Data

US 2019/0336047 A1    Nov. 7, 2019

Related U.S. Application Data

(60) Provisional application No. 62/664,642, filed on Apr. 30, 2018.

(51) Int. Cl.
| | | |
|---|---|---|
| *A61B 5/12* | (2006.01) | |
| *A61B 5/00* | (2006.01) | |
| *A61B 5/38* | (2021.01) | |

(52) U.S. Cl.
CPC .............. *A61B 5/125* (2013.01); *A61B 5/38* (2021.01); *A61B 5/4047* (2013.01); *A61B 5/4052* (2013.01); *A61B 5/7217* (2013.01)

(58) Field of Classification Search
CPC ............ A61N 1/36103; A61N 1/36036; A61N 1/36038; A61N 1/3606; A61N 1/36135; A61N 1/36139; A61B 5/4052; A61B 5/4041; A61B 5/11; A61B 5/486; A61B 5/6803; A61B 5/38; A61B 5/377; G06F 3/015

See application file for complete search history.

(56) References Cited

U.S. PATENT DOCUMENTS

| | | | |
|---|---|---|---|
| 8,241,224 B2 * | 8/2012 | Keefe | ................... A61B 5/121 |
| | | | 600/559 |
| 2012/0302859 A1 | 11/2012 | Keefe | |
| 2013/0303941 A1 | 11/2013 | Porges et al. | |
| 2016/0256083 A1 | 9/2016 | Lodwig et al. | |

OTHER PUBLICATIONS

Aug. 16, 2019—(PCT) ISR and WO—App PCT/US19/30027.

(Continued)

*Primary Examiner* — Deborah L Malamud
(74) *Attorney, Agent, or Firm* — Banner & Witcoff, Ltd.

(57) ABSTRACT

The present disclosure describes systems and methods to evaluate auditory efferent function by exposing a patient to short-duration acoustic click stimuli to generate a click-evoked otoacoustic emission (CEOAE) occurring in each ear of the patient, and in response to exposing the patient to click stimuli, concurrently sampling outer hair cell activity (OHC) and medial olivocochlear reflex (MOCR; efferents) in each ear of the patient, monitoring the middle ear muscle reflex (MEMR) in each ear of the patient, and measuring a change in cochlear activity in the patient based on the CEOAE, MOCR, and MEMR of each ear of the patient.

11 Claims, 10 Drawing Sheets

(56) References Cited

OTHER PUBLICATIONS

Guinan, Olivocochlear Efferents: Anatomy, Physiology, Function, and the Measurement of Efferent Effects in Humans, 2006. Ear Hear, 27(6), 589-607.
Maison et al., Predicting Vulnerability to Acoustic Injury with a Noninvasive Assay of Olivocochlear Reflex Strength, 2000, J Neurosci, 20(12), 4701-4707.
Veuillet et al., Auditory processing disorder in children with reading disabilities: effect of audiovisual training, 2007, Brain, 130(11), 2915-2928.
Wilson et al., Efferent inhibition strength is a physiological correlate of hyperacusis in children with autism spectrum disorder, 2017, J Neurophysiol, 118: 1164-1172, 2017.
Mertes et al., Within- and Across-Subject Variability of Repeated Measurements of Medial Olivocochlear-Induced Changes in Transient-Evoked Otoacoustic Emissions, 2016, Ear Hear, 37(2), e72-e84.
Mishra et al., Repeatability of Click-Evoked Otoacoustic Emission-Based Medial Olivocochlear Efferent Assay, 2013, Ear Hear, 34(6), 789-798.
Abdala et al., Aging of the medial olivocochlear reflex and associations with speech perception, 2014, JASA, 135(2), 754-765.
Liberman et al., The ipsilaterally evoked olivocochlear reflex causes rapid adaptation of the 2 f1f2 distortion product otoacoustic emission, 1996, JASA, 99(6), 3572-3584.
Backus et al., Time-course of the human medial olivocochlear reflex, 2006, JASA, 119(5), 2889-2904.
Boothalingam et al., Click-Evoked Auditory Efferent Activity: Rate and Level Effects, 2018, JARO, 19(4): 421-434.
Winslow et al., Effect of Electrical Stimulation of the Crossed Olivocochlear Bundle on Auditory Nerve Response to Tones in Noise, 1987, J. Neurophysiology, 57(4), 1002-1021.

\* cited by examiner

SIMULTANEOUS ESTIMATION OF COCHLEAR AND EFFERENT ACTIVITY

RELATED APPLICATION DATA

This application claims benefit to U.S. Provisional Application No. 62/664,642, filed on Apr. 30, 2018 and hereby incorporated by reference in its entirety.

TECHNICAL FIELD

Aspects of the present disclosure relate to the measurement of otoacoustic emissions and/or acoustic signals generated in the cochlea, and the magnitude and time course of efferent neural activity elicited by an auditory stimulus.

BACKGROUND

The auditory efferent system is thought to aid in multiple hearing functions, but its functional and clinical relevance is poorly understood. One major reason for this paucity in knowledge is the lack of a standardized measurement tool that can be used to evaluate the function of the auditory efferent system. For example, measurements of the auditory efferent system, typically restricted to laboratories, involve application of noise in the ear opposite to the test ear (contralateral ear) and measurement of change in cochlear activity in the test ear. Such a methodology is limited in that it does not test the entire efferent system (i.e., both ears and both halves of the efferent neural circuit).

SUMMARY

The present disclosure addresses the need to test the entire efferent system and is based on the discovery that the auditory efferent system, especially the medial olivocochlear reflex (MOCR), is implicated in both typical auditory processing and in auditory disorders. The present disclosure describes methods and systems to elicit the MOCR bilaterally (i.e., both ears and both halves of the efferent neural circuit).

According to one aspect, the present disclosure provides a method to evaluate auditory efferent function by exposing a patient to short-duration acoustic activator click stimuli to generate a click-evoked otoacoustic emission (CEOAE) occurring in each ear of the patient, and in response to exposing the patient to activator click stimuli, concurrently sampling outer hair cell (OHC) activity and the medial olivocochlear reflex (MOCR) in each ear of the patient, monitoring the middle ear muscle reflex (MEMR) in each ear of the patient, and measuring a change in cochlear activity in the patient based on the CEOAE, MOCR, OHC, and MEMR of each ear.

According to another aspect, the present disclosure provides a system operable to monitor and evaluate auditory efferent function of a patient. In certain aspects, the system may include a processing device, wherein the processing device is configured to generate and expose a patient to a short-duration acoustic activator click stimuli to generate a click-evoked otoacoustic emission (CEOAE) in each ear of the patient, wherein the processing device is configured to concurrently sample outer hair cell activity (OHC) and medial olivocochlear reflex (MOCR "the efferent activity") in each ear of the patient in response to exposing the patient to the short-duration acoustic activator click stimuli. In other aspects, the system processing device may be configured to monitor the middle ear muscle reflex (MEMR) in each ear of the patient, and the processing device may be configured to measure a change in cochlear activity in the patient based on the CEOAE, the efferent activity, and the MEMR of each ear. The system may also include a first probe and a second probe, wherein the first and the second probes are configured to transmit the activator click stimuli to each ear of the patient, and wherein the first and the second probes are configured to detect, monitor, and record the CEOAE, the MEMR, and the efferent activity of each ear of the patient. In other aspects, the system may also include a user interface and a monitor.

According to yet another aspect, the present disclosure describes one or more non-transitory computer-readable media having instructions stored thereon that when executed, cause at least one processing device to (1) generate a short-duration acoustic activator click stimuli to generate a click-evoked otoacoustic emission (CEOAE) occurring in each ear of a patient; (2) sample outer hair cell activity (OHC) and medial olivocochlear reflex (MOCR) in each ear of the patient; (3) monitor middle ear muscle reflex (MEMR) in each ear of the patient; and (4) measure the change in cochlear activity in the patient based on the CEOAE, MOCR, and MEMR of each ear.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

The brain enables the selective processing of relevant auditory information using various feedback networks of the nervous system. One such feedback connection, the medial olivocochlear reflex (MOCR), reaches the ear from the brain, and is involved in regulating inner ear activity. The result of this regulatory function of MOCR is mediation in a variety of hearing-related tasks. It mediates attention from the cortex to the ear by dynamically and selectively inhibiting inner ear activity. More importantly, the MOCR plays an oto-protective role against the deleterious effects of noise on the inner ear. In relation to noise or ageing related damage, the MOCR strength has predictive, prognostic, and diagnostic value. Predictive: evidence in animal models suggests a link between individual MOCR strength and 'toughness' against noise damage and the ability to listen in noisy environments. Prognostic: the MOCR neural loss precedes the loss in hearing that is associated with ageing. Diagnostic: the MOCR may also reflect early changes in the brain resulting from increased noise exposure, in addition, some human studies have also implicated a clinical role of the MOCR in auditory disorders such as auditory neuropathy, where firing patterns of the auditory nerve response are affected. Other studies have shown weaker MOCR function in children with certain developmental disorders. Finally, measuring the MOCR may be of value in detecting general peripheral synaptopathy/neuropathy in the auditory system, often referred to as "hidden hearing loss."

Taken together, quantifying MOCR function can provide a wealth of clinical information that will both establish the status of inner ear and auditory neural function, as well as predict susceptibility to noise damage. Despite such compelling evidence on the clinical relevance of MOCR, a standard test of MOCR currently does not exist.

Typical methods used to study MOCR in humans involves measuring the change in cochlear activity during MOCR activation using otoacoustic emissions (OAEs). OAEs are runaway energy that are generated during the active amplification process of the outer hair cells (OHCs) in the inner ear. Because the MOCR innervation of OHCs is inhibitory, measuring a reduction in OHC activity using OAEs has proven to be an effective non-invasive tool in quantifying the MOCR.

However, several issues must be addressed before an OAE-based method can be used in the clinic. More specifically, test-retest reliability of current methods is rather poor. Further, clinical use has been limited by methodological complications such as calibration of stimuli, inadvertent activation of the middle ear muscle reflex (MEMR) (an effect that can masquerade as an MOCR effect), and attentional state of the participant. In addition, current methods only test one side of the (contralateral) MOCR neural pathway while MOCR neurons project bilaterally to both ears. This is because current methods rely on noise stimuli to elicit MOCR activity while OAEs monitor MOCR-induced changes in the opposite (contralateral) ear. Exacerbating this situation is the fact that investigators use vastly different OAE-based paradigms to study the MOCR, rendering comparisons across studies onerous. Finally, current methods oversimplify the MOCR effect on OAEs by reporting a single level-change value, thereby reducing the power of the method and succumbing to unexplained variabilities. We have developed a method that offers simple yet powerful solutions to all the aforementioned methodological issues. We use a short-duration acoustic stimulus (clicks) to concurrently sample OHC and MOCR activity while also monitoring the MEMR. Further, by not using the typical noise-based MOCR paradigms, we are also able to elicit the bilateral MOCR, i.e., from both ears simultaneously. We also monitor click-evoked MOCR across time, and as such, our data is not limited to a single level-change value, rather a rich time-course of the MOCR is obtained. The time-course is resilient to factors (e.g., attention, stimulus level) that cause large variability in the simple level-change metric. Taken together, our novel MOCR method overcomes all shortcomings that affect current MOCR methods, rendering the disclosed method probably the first clinically feasible test of MOCR.

Major implications of a clinical MOCR test is in its predictive, prognostic, and diagnostic abilities. For instance, an MOCR test can be used by the army to identify individuals with weak MOCR as they are more likely to develop noise-induced hearing loss, and are less likely to pick key information over radio in noisy environments. Because soldiers in combat zones rely on radio communication (degraded speech) in noisy environments, individuals with stronger MOCR may be better suited for such key roles. Further, the inclusion of MOCR test in the test batteries for developmental disorders will be a valuable diagnostic marker. Emerging evidence suggests that an MOCR test may also be useful in identifying atypical neural function in the brain (e.g., autism, hyperacusis). Dissemination of the newly developed tool to clinicians and scientists will widen the horizons of an MOCR test for both clinical populations and improving our understanding the auditory brain.

One prior invention, described in U.S. patent application Ser. No. 15/134,657, discloses a method using clicks to elicit MOCR, but rely on presenting the clicks in the contralateral ear to activate the MOCR. In addition, this method relies on the conventional block averaging and forward masking where a buffer of CEOAEs, without-MOCR activation, and a buffer of CEOAE, with MOCR activation, are compared to calculate the MOCR strength. Notwithstanding the use of clicks rather than noise to elicit MOCR, this prior art approach is prone to the same pitfalls of conventional methods that use noise to elicit MOCR. The present disclosure is fundamentally different from the prior art because the present disclosure circumvents the use of a separate MOCR elicitor, be it noise or clicks, and uses the OAE evoking clicks to also elicit MOCR and concurrently measure OHC as well as efferent activity. A major innovation in the present disclosure is also the ability to extract efferent time-course using activator clicks alone.

Aspects of the present disclosure involve a clinical test of MOCR that considers all the limitations of current methods. In various aspects, the disclosed system and method uses acoustic clicks, instead of noise, which allows for simultaneous estimation of both cochlear and efferent activity while monitoring MEMR. This is because, clicks evoke both cochlear otoacoustic emissions (OAEs)—a measure of cochlear activity/health and also the efferent system (including the MOCR). In fact, we found that typical usage of clicks to study only the cochlea also evokes the efferent system, obscuring a true estimate of cochlear health. The disclosed method uses this phenomenon to our advantage by simultaneously estimating MOCR activity along with click-evoked OAEs. As such, the disclosed method will also improve click OAE measures from newborn hearing screening to other diagnostic applications in audiology. The major innovation in this method is tracking the time-course of the MOCR induced change in CEOAEs concurrently in both ears along with the more traditional estimation of magnitude of change. Our method preserves the time-course by "vertically" averaging trains of CEOAEs (1-2 second in duration) instead of averaging all CEOAEs into a single pool in 1-2 second blocks. Time-course and level-change are then obtained by statistical line-fits to the vertically averaged CEOAE data by averaging the entire block of CEOAEs. Time-course provides a robust measure of efferent activity as it is not influenced by variables that affect the CEOAE level-change metric that is currently in use. The method disclosed here specifically involves the use of click trains of in three modes. (1) Using at least two rates and levels, wherein the faster and more intense click train activates the efferents as well as monitors the efferent activity. The slower and less intense clicks serve as baselines as well as capture the decaying time-course of the efferent system. Preferred parameters for the activator clicks (faster clicks) are of levels between 65 and 90 dB peak-to-peak equivalent sound pressure level (ppeSPL) and of rates between 50 and 75 Hz over a time-course of 0.25-2 seconds. In some examples, the parameters for the activator clicks are of levels between 50 and 90 dB peak-to-peak equivalent sound pressure level (ppeSPL) and of rates between 20 and 75 Hz over a time-course of 0.25-2 seconds. In addition, slower clicks may be included to capture the recovery of the reflexes. The parameters for these clicks include activation levels and rates of about 50 to 65 dB ppeSPL and 5 to 20 Hz over at least 0.3-1 second. In some examples, the preferred click parameters are at least 55 dB and at least 20 Hz over at least 0.3 seconds, and/or at least 80 dB ppeSPL and at least 10 Hz over at least 0.6 seconds. In other examples, the click levels are at least 50 dB, 55 dB, 60 dB, 65 dB, 70 dB, 75 dB, 80 dB, 85 dB, 90 dB, 95 dB, 100 dB, or 105 dB. In still other examples, the click rates are at least 40 Hz, 45 Hz, 50 Hz, 55 Hz, 60 Hz, 65 Hz, 70 Hz, 75 Hz, 80 Hz, 85 Hz, 90 Hz, 95 Hz, or 100 Hz. In yet other examples, the time-course is at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 seconds. In an alternate approach, a single series of activator clicks can be used to estimate the MOCR and monitor the MEMR. In this approach, the CEOAE recorded for the first few clicks serve as the baseline with the magnitude of the MOCR estimated as the change from this baseline to the level of CEOAE recorded for clicks presented later in the series. This approach allows for a slightly faster estimation of the time-course at the cost of a slightly reduced time resolution. Finally, all CEOAEs can be used to generate a robust template of the CEOAE. The template CEOAE will be compared across all CEOAEs in the 0.25-2 second time-course, vertically averaged, block averaged to calculate the magnitude of the CEOAE at each time-point. By leveraging all available clicks, this approach allows for the fastest estimation of CEOAEs, efferent magnitude and monitoring MEMR while still preserving the time-course of the efferents. In all the above described modes, comparison across CEOAEs within the 0.25-2 second activator window may be based on a change in either the (1) magnitude in the time domain, (2) magnitude and phase in the Fourier transformed frequency domain, or (3) magnitude and phase in the time-frequency domain. A silent interval of at least 0.25 seconds may be required to reset the efferent system to its baseline functioning. In all cases, the disclosed parameters provide an optimal rate-level combination that evokes measurable efferent modulation of CEOAEs.

The disclosed method for estimating the auditory efferents provides a complete picture of all three literalities of the system when the faster clicks in one ear are combined with the slower clicks in the opposite ear, therefore, allowing for calculation of binaural interaction of the auditory efferents. In addition, accurate estimation of the efferent influence on cochlear activity measured using click-evoked OAEs allows for correction of OAE level. This will provide an accurate estimate of cochlear health, in addition to determining the efferent health. This claim is backed by a comprehensive study of click-evoked OAE measured by varying multiple measurement parameters.

Figure 1:
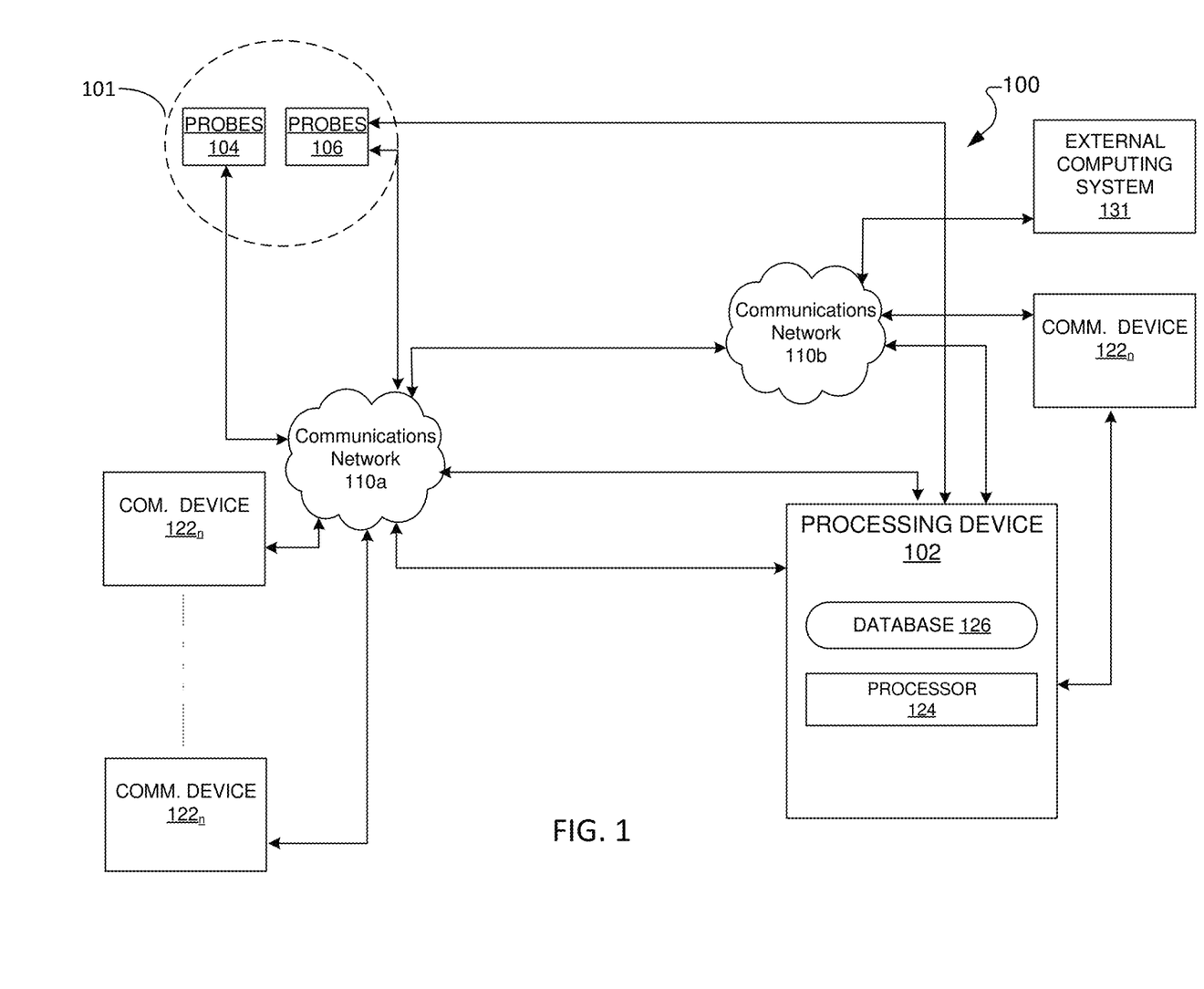
FIG. 1 is a block diagram illustrating computing environment for producing auditory stimuli and evaluating auditory efferent function, according to aspects of the present disclosure.

Referring now to the Figures—FIG. 1 illustrates a computing architecture 100 capable of automatically evaluating auditory efferent function in humans, according to aspects of the present disclosure. As illustrated, the computing architecture 100 includes a processing device 102 (e.g., a server computing device) capable of executing various signal processing algorithms and instructions that evaluate auditory efferent function in humans. Thus, as illustrated, the processing device 102 provides or otherwise generates auditory stimulus and records response signals (as will be described in detail below) from probes 104 and 106 located, for example, in the two ears of a patient 101. Probes 104 and 106 may contain up to three miniature loudspeakers and at least one microphone. The loudspeakers present the click-stimulus and the microphone records the ear canal sound pressure level that includes the click-stimulus and the click-evoked otoacoustic emission (CEOAE). The processing device 102 may further process the recorded signals to evaluate the auditory efferent function in humans. The processing device 102 includes a database 124 and a processor 130. The database 220 may be a database, data store, storage and/or the like, for storing data involved in evaluating auditory efferent function in humans. In one specific example, the database 124 may store data involving OAEs, MOCR, MEMR, and/or the like.

The processing device 102 may communicate through one or more networks 110a, 110b. The one or more networks may be an IP-based telecommunications network, the Internet, an intranet, a local area network, a wireless local network, a content distribution network, or any other type of communications network, as well as combinations of networks. For example, in one particular embodiment, the networks 110a and 110b may be a telecommunications network including fiber-optic paths between various network elements, such as servers, switches, routers, and/or other optical telecommunications network devices that interconnect to enable receiving and transmitting of information between the various elements as well as users of the network.

The processing device 102 may functionally connect or otherwise communicate (e.g., using the one or more networks 110a, 100b) with communication devices ($122_1$, $122_2$, ..., $122_n$) included within the computing environment 100. The communication devices ($122_1$, $122_2$, ..., $122_n$) included within the computing environment 100 may be used to remotely interface with the probes 104-106 and/or the processing device 102 when generating auditory stimulus for transmission to probes 104 and 106 and recording signals from probes 104 and 106. The communication devices ($122_1$, $122_2$, ..., $122_n$) may be any of, or any combination of, a personal computer; handheld computer; mobile phone; digital assistant; smart phone; server; application; and the like. In one embodiment, each of the communication devices ($122_1$, $122_2$, ..., $122_n$) may include a processor-based platform that operates on any suitable operating system, such as Microsoft® Windows®, Linux®, Android®, iOS® and/or the like that is capable of executing software processes, software, applications, etc. The communication devices ($122_1$, $122_2$, ..., $122_n$) devices may also include a communication system to communicate with the various components of the computing environment 100 via a wireline and/or wireless communications, such as networks 110a, 100b.

Figure 2:
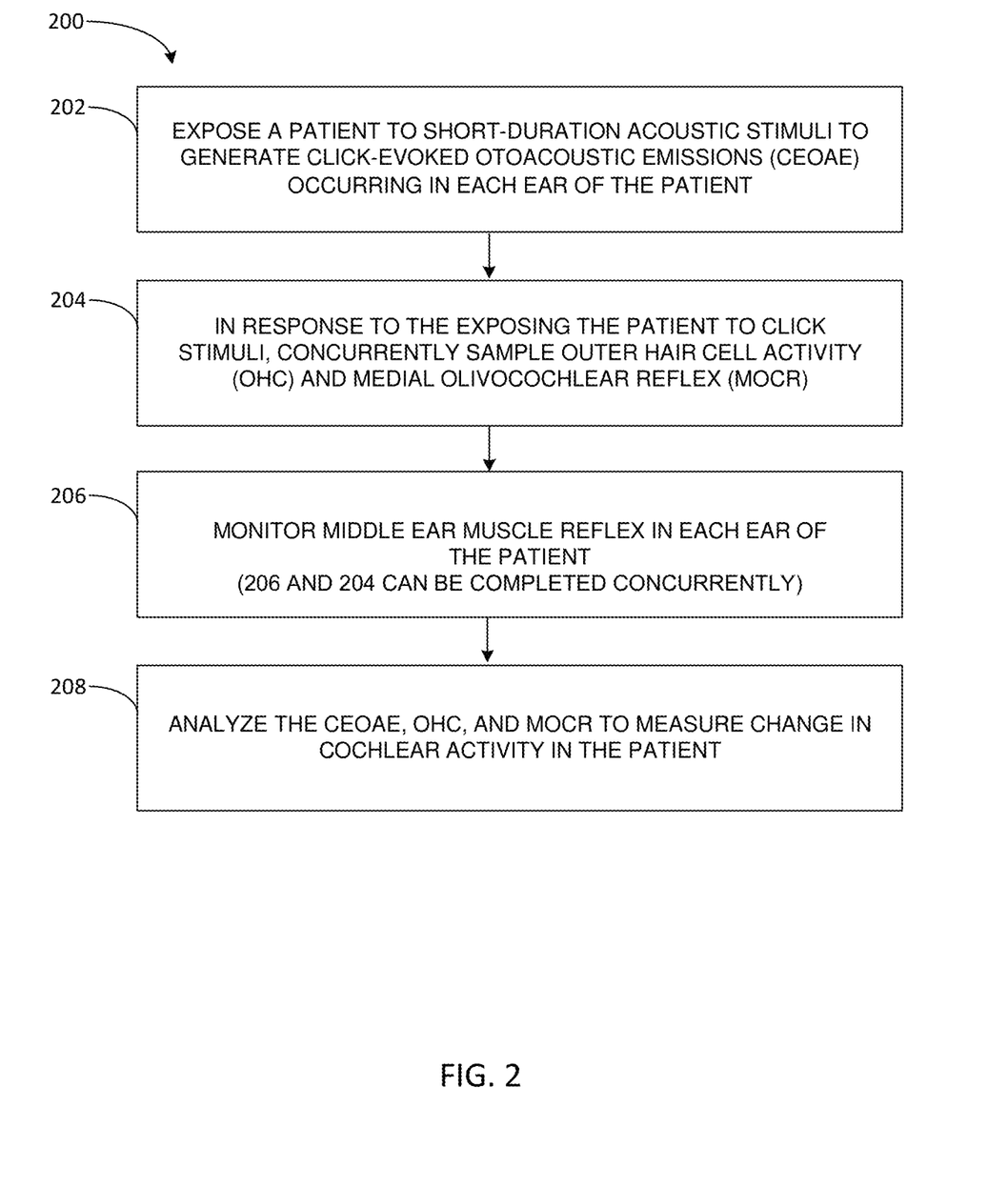
FIG. 2 is a flowchart for evaluating change in cochlear activity during medial olivochlear reflex activation, according to aspects of the present disclosure.

Referring now to FIG. 2 and with reference to FIG. 1, an illustrative process 200 for evaluating auditory efferent function in humans is provided. As illustrated, process 200 begins at 202, with exposing a patient to short-duration acoustic stimuli (click-stimuli) to generate click-evoked otoacoustic emission (CEOAE) occurring in each ear of the patient. At 204, in response to exposing the patient to click stimuli, OHC and MOCR activity is sampled concurrently while also monitoring MEMR. At 208, the CEOAE, an estimate of cochlear (specifically, the OHC) functioning, and MOCR of each ear, is analyzed to measure the change on cochlear activity in the patient.

Aspects of the present disclosure also involve the usage of algorithms to acquire robust CEOAEs to allow reliable quantification of the efferent magnitude within the 0.25-2 second activator window in the shortest possible time, i.e., mode-3 as previously described. This is achieved by dynamic stopping rules that automatically stop the efferent test based on: (1) a criterion number of click-stimuli presentations and/or (2) achieving a criterion CEOAE signal-to-noise ratio and/or (3) achieving a significance on a set of signal processing and statistical criteria that compares successive CEOAEs with prior block averages.

Figure 3:
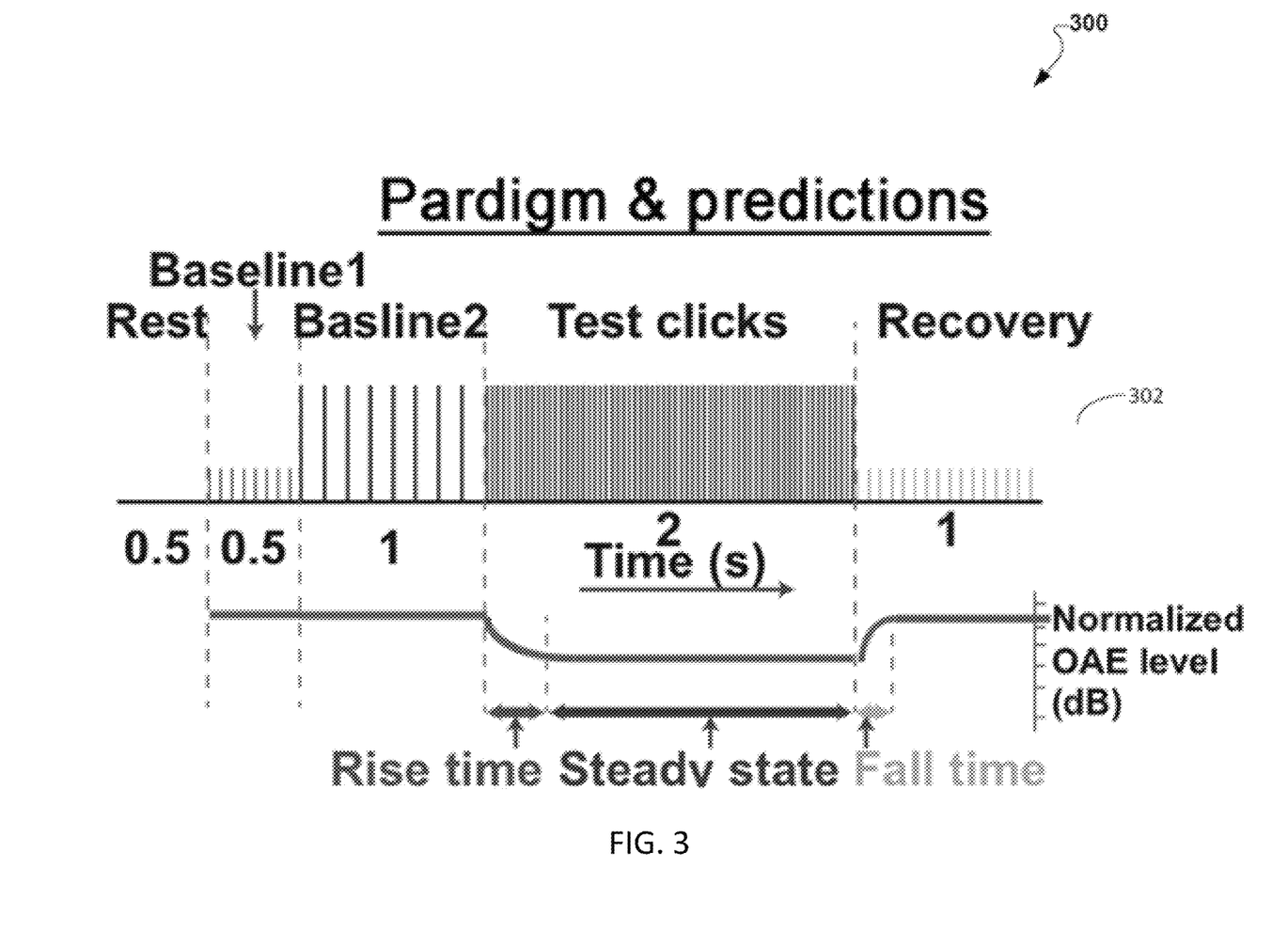
FIG. 3 is an illustration of an example measurement of a time course of MOCR activity, according to aspects of the present disclosure.
Figure 5:
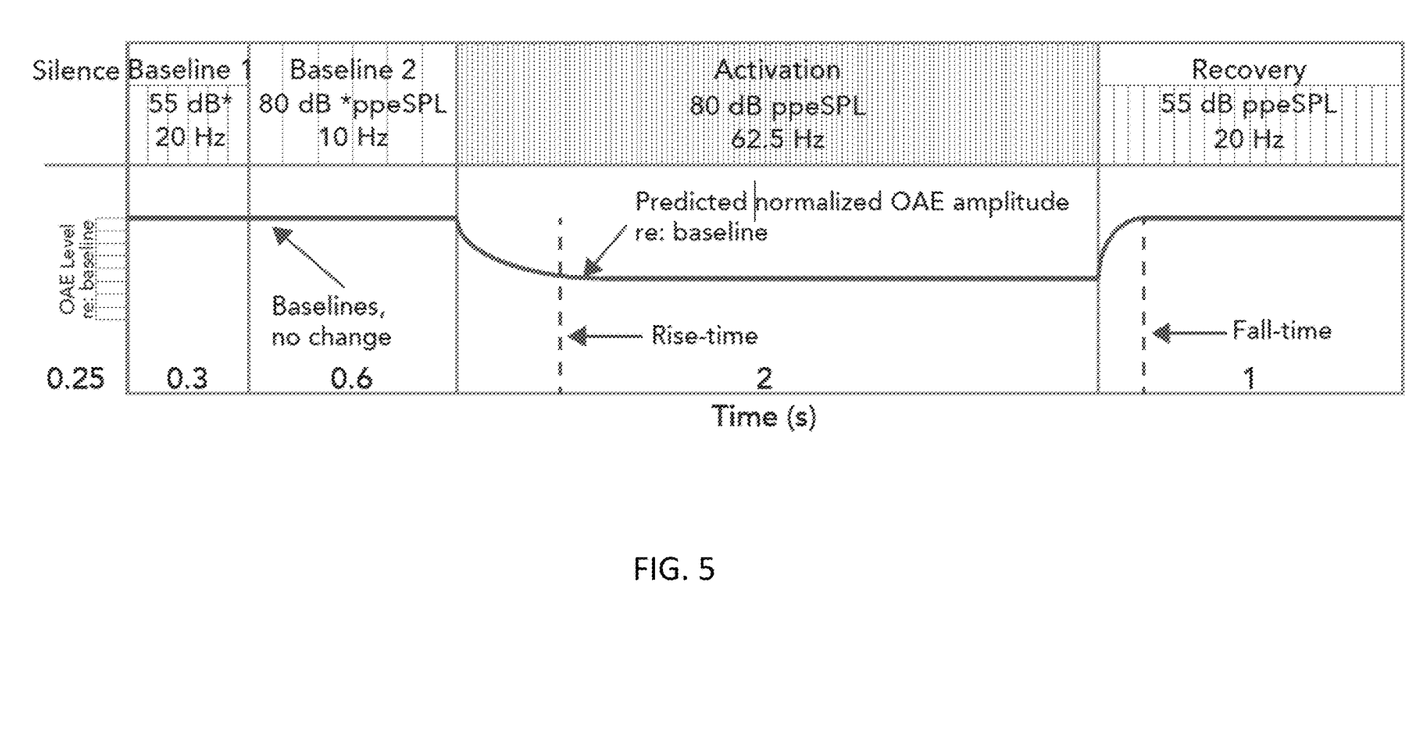
FIG. 5 is an illustration of an example CEOAE-based efferent paradigm showing MOCR (using OAEs between 0.8 and 5 kHz) and MEMR (using stimulus between 0.8 and 1.2 kHz) monitored in the activation and recovery windows to calculate rise and fall times (time constants) and magnitude (change with respect to the baseline), respectively using double-exponential fits. An example short-duration acoustic stimuli activation levels are about 80 dB peak-to-peak peak equivalent sound pressure level (ppeSPL) at the rate of 62.5 Hz over a time-course of 2 seconds is illustrated, according to aspects of the present disclosure.

FIG. 3 illustrates an example measurement of a time course of MOCR activity 300, according to one aspect of the present disclosure. As illustrated at 302, the time course of the MOCR-induced change in CEOAEs in both ears may be tracked and the time course may be preserved by "vertically" averaging trains of CEOAEs (e.g., 1-2 second in duration) instead of averaging all CEOAEs into a single pool. This can be done by taking into consideration the slower-rate and low-level clicks. Alternatively, FIG. 5 illustrates using the first few activator clicks as baseline to extract the time-course of the MOCR without the need for slower-rate and low-level clicks. At 304, time-course and level-change may then be obtained using statistical line-fits to the vertically averaged CEOAE data. Time-course provides a robust measure of efferent activity as it is not influenced by variables that affect the CEOAE level-change metric that is currently in use. Appendix A entitled, "Click-Evoked Auditory Efferent Activity: Rate and Level Effects" (see Boothalingam, S., Kurke, J. & Dhar, S., 2018. *JARO*, 19(4): 421-434) discussed various methods for evaluating auditory efferent function and is incorporated by reference in its entirety herein.

Figure 4:
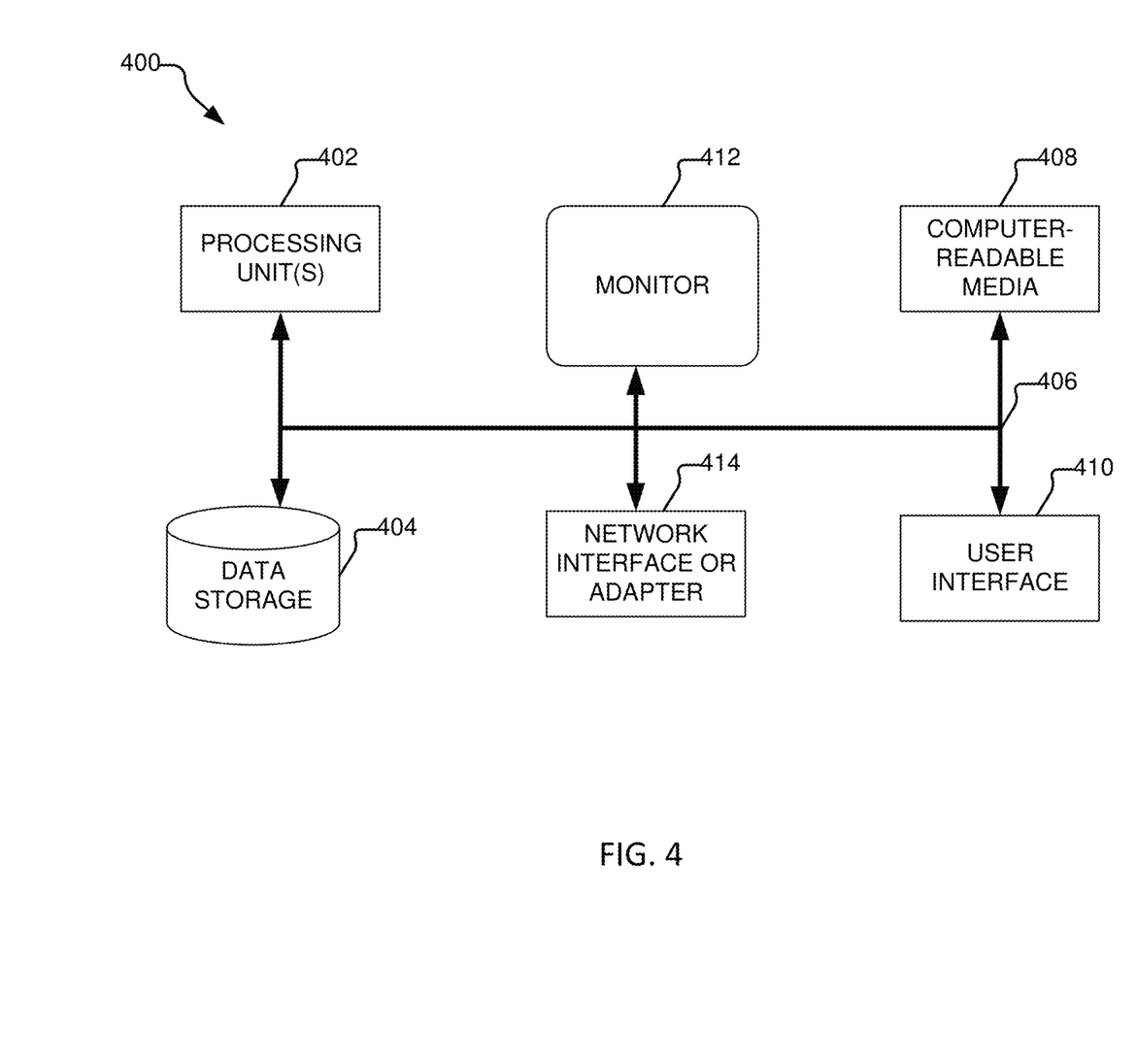
FIG. 4 is a block diagram illustrating a computing device, according to aspects of the present disclosure.

FIG. 4 illustrates an example of a suitable computing and networking environment 400 that may be used to implement various aspects of the present disclosure described in FIGS. 1-2. As illustrated, the computing and networking environment 400 includes a general purpose computing device 400, although it is contemplated that the networking environment 400 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 400 may include various hardware components, such as a processing unit 402, a data storage 404 (e.g., a system memory), and a system bus 406 that couples various system components of the computer 400 to the processing unit 402. The system bus 406 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 400 may further include a variety of computer-readable media 408 that includes removable/non-removable media and volatile/nonvolatile media, but excludes transitory propagated signals. Computer-readable media 408 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 400. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 404 includes computer storage media in the form of volatile/nonvolatile memory such as read only memory (ROM) and random access memory (RAM). A basic input/output system (BIOS), containing the basic routines that help to transfer information between elements within the computer 400 (e.g., during start-up) is typically stored in ROM. RAM typically contains data and/or program modules that are immediately accessible to and/or presently being operated on by processing unit 402. For example, in one embodiment, data storage 404 holds an operating system, application programs, and other program modules and program data.

Data storage 404 may also include other removable/non-removable, volatile/nonvolatile computer storage media. For example, data storage 404 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 4, provide storage of computer-readable instructions, data structures, program modules and other data for the computer 400.

A user may enter commands and information through a user interface 410 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 402 through a user interface 410 that is coupled to the system bus 406, but may be connected by other interface and bus structures, such as a parallel port, game port or a universal serial bus (USB). A monitor 412 or other type of display device is also connected to the system bus 406 via an interface, such as a video interface. The monitor 412 may also be integrated with a touch-screen panel or the like.

The computer 400 may operate in a networked or cloud-computing environment using logical connections of a network interface or adapter 414 to one or more remote devices, such as a remote computer. The remote computer may be a personal computer, a server, a router, a network PC, a peer device or other common network node, and typically includes many or all of the elements described above relative to the computer 400. The logical connections depicted in FIG. 4 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 400 may be connected to a public and/or private network through the network interface or adapter 414. In such embodiments, a modem or other means for establishing communications over the network is connected to the system bus 406 via the network interface or adapter 414 or other appropriate mechanism. A wireless networking component including an interface and antenna may be coupled through a suitable device such as an access point or peer computer to a network. In a networked environment, program modules depicted relative to the computer 400, or portions thereof, may be stored in the remote memory storage device.

The following example is set forth as being representative of the present disclosure. This example is not to be construed as limiting the scope of the present disclosure as this and other equivalent embodiments will be apparent in view of the present disclosure, figures and accompanying claims.

Example I

Clinical Test of the Auditory Efferent System

As discussed above, the auditory efferent system is implicated in both typical auditory processing and in auditory disorders. But the clinical applicability of the MOCR is currently under-utilized. This is, in part, because the repeatability of conventional MOCR tests is rather low. Conventional tests employ broadband noise in one ear while monitoring change in OAEs in the other ear to index efferent activity. Such conventional assays (1) are limited in their ability to assay only the contralateral MOCR pathway, (2) risk activating the MEMR, and (3) are unable to extract the kinetics (time-course) of the reflexes. The example described below repurposes the same OAE-evoking click train to also concurrently elicit the MOCR bilaterally. Data from click-train presentation at 80 dB peak-to-peak peak equivalent sound pressure level (ppeSPL) in 14 young normal hearing adults demonstrate the feasibility of the above disclosed methods and systems. Mean MOCR magnitude (~2 dB) and activation time-constant (200-250 ms) corroborate prior MOCR reports. The data described below also suggests several advantages of the novel method including, (1) the ability to monitor MEMR, (2) obtain both magnitude and kinetics of the MOCR (time constants), and (3) a potential reduction in test-time based on the application of statistical stopping rules.

Sample size included 14 young (18-30 yrs; Mage±SDage=21±2 yrs; 1 male) typical hearing adult volunteers, confirmed by standard audiologic procedures. A total of 20 individuals were tested, 6 were rejected due to MEMR activation (n=2), excessive artifacts (n=3), an influence of spontaneous OAEs (n=1). Reflex threshold (226 Hz probe; GSI Tympstar) for clicks presented at 100 Hz (>90 dB HL thresholds were considered as 110 dB HL).

| Ipsilateral Ear | Mean ± SD (dB HL) | Min, Max (dB HL) |
|---|---|---|
| Right | 96 ± 15 | 65, 110 |
| Left | 91 ± 14 | 70, 110 |

Stimulus and experimental paradigm included clicks used to both evoke OAEs and elicit the efferent MOCR in the paradigm shown in FIG. 5. This was repeated 500 times to obtain mean OAEs from 1000 clicks (two adjacent clicks were averaged) for ipsilateral, contralateral, and bilateral conditions (as previously described in mode-2).

Figure 6:
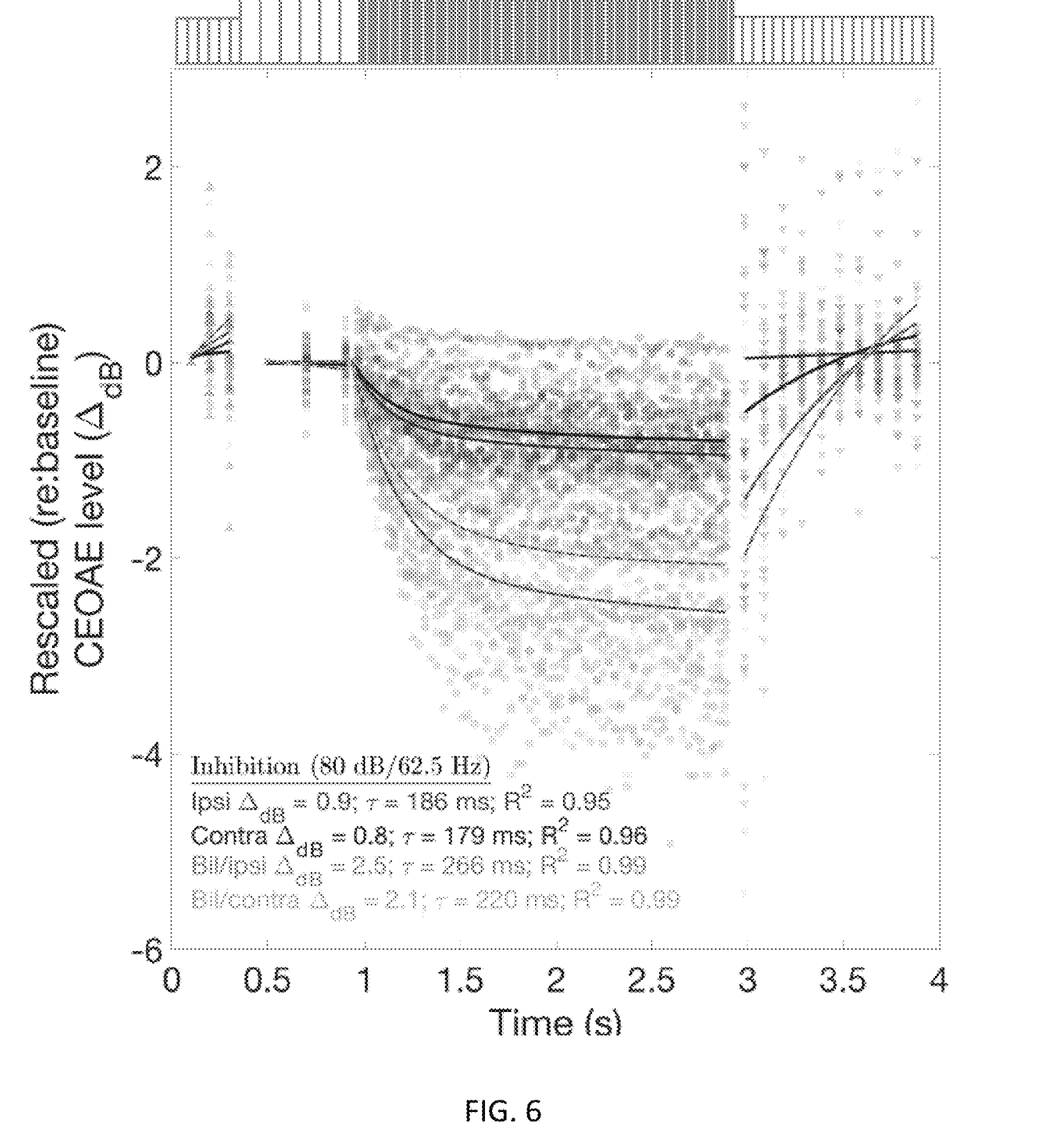
FIG. 6 is an illustration MOCR time course showing the change in the CEOAE level (MOCR magnitude, ΔdB) across time for ipsilateral, contralateral, and bilateral activations according to aspects of the present disclosure.
Figure 7:
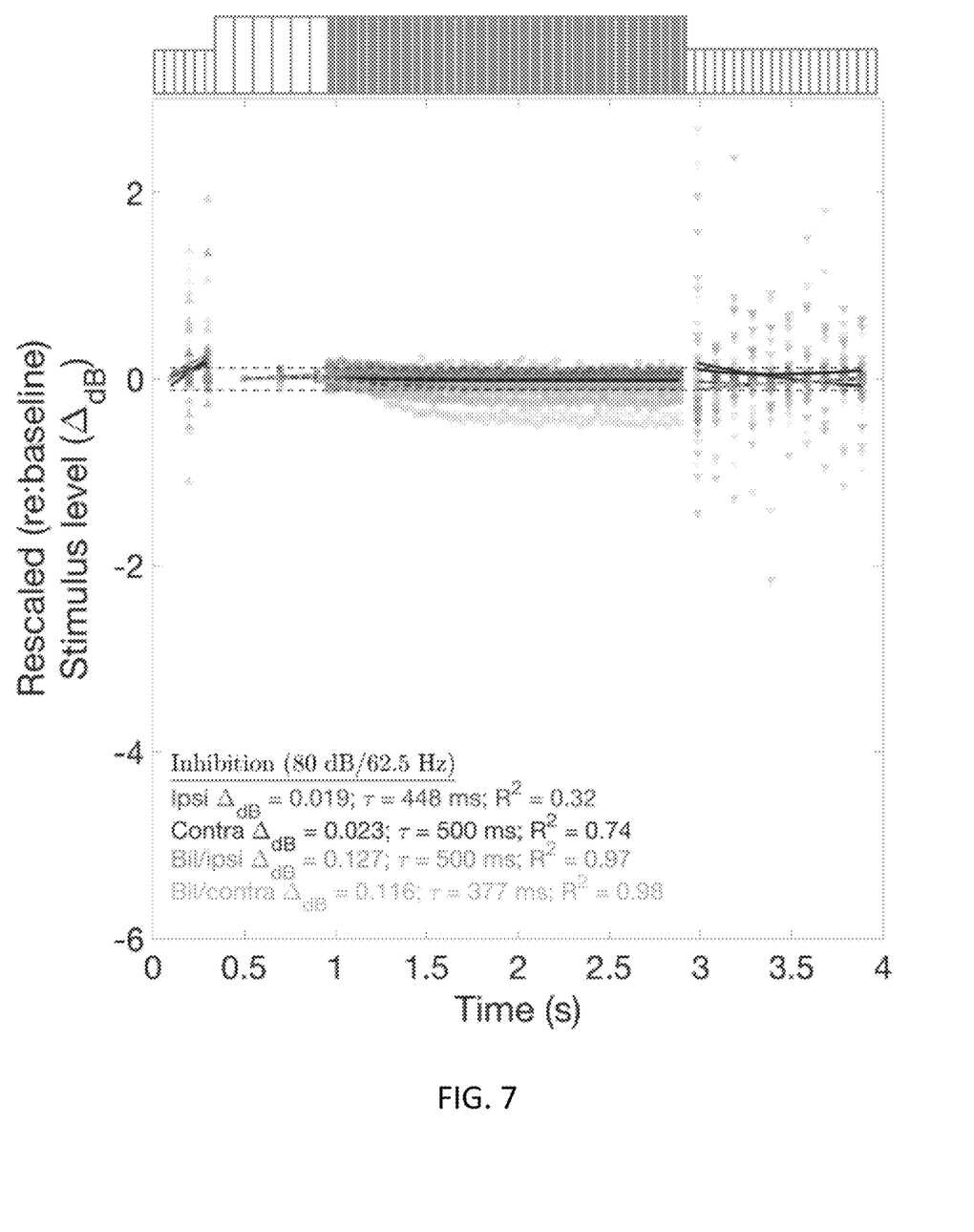
FIG. 7 is an illustration MEMR time course showing the change in the click stimulus level across time according to aspects of the present disclosure.
Figure 8:
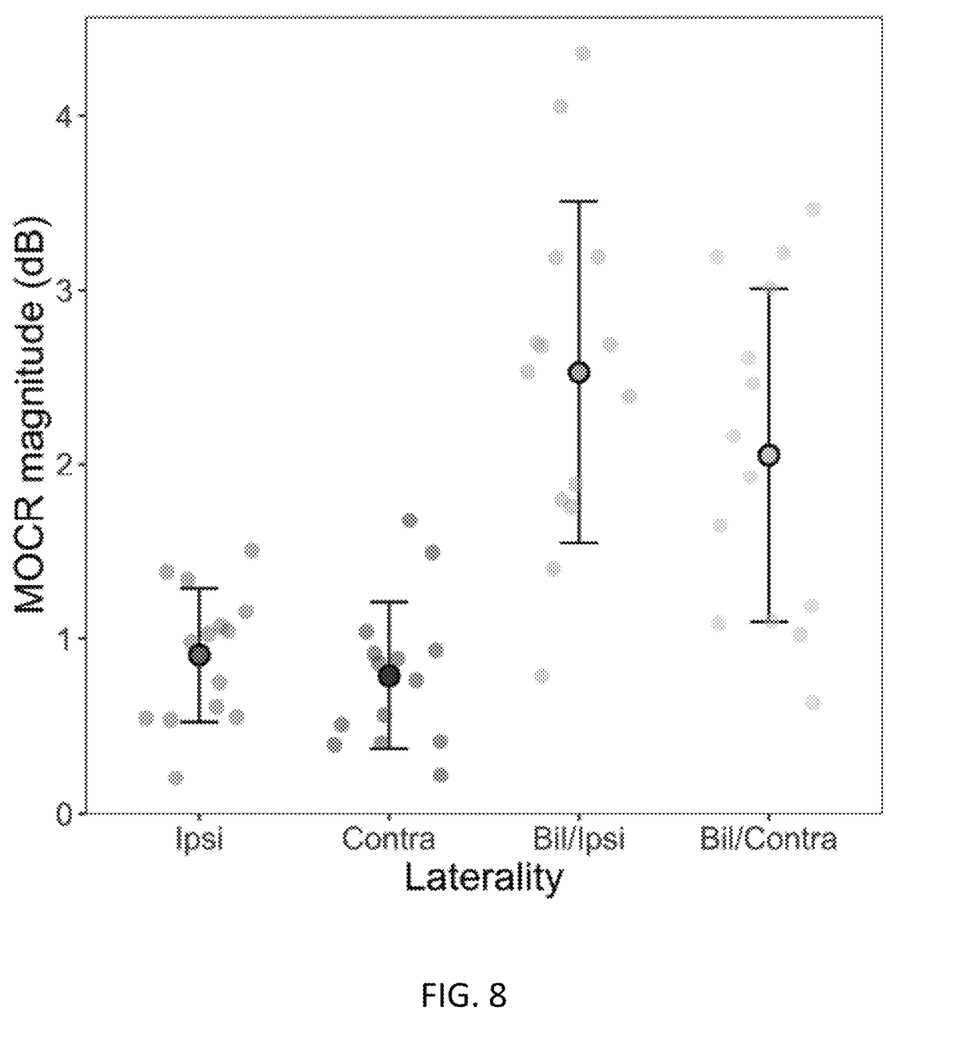
FIG. 8 illustrates MOCR magnitude (ΔdB) across laterality in the activator window according to aspects of the present disclosure.
Figure 9:
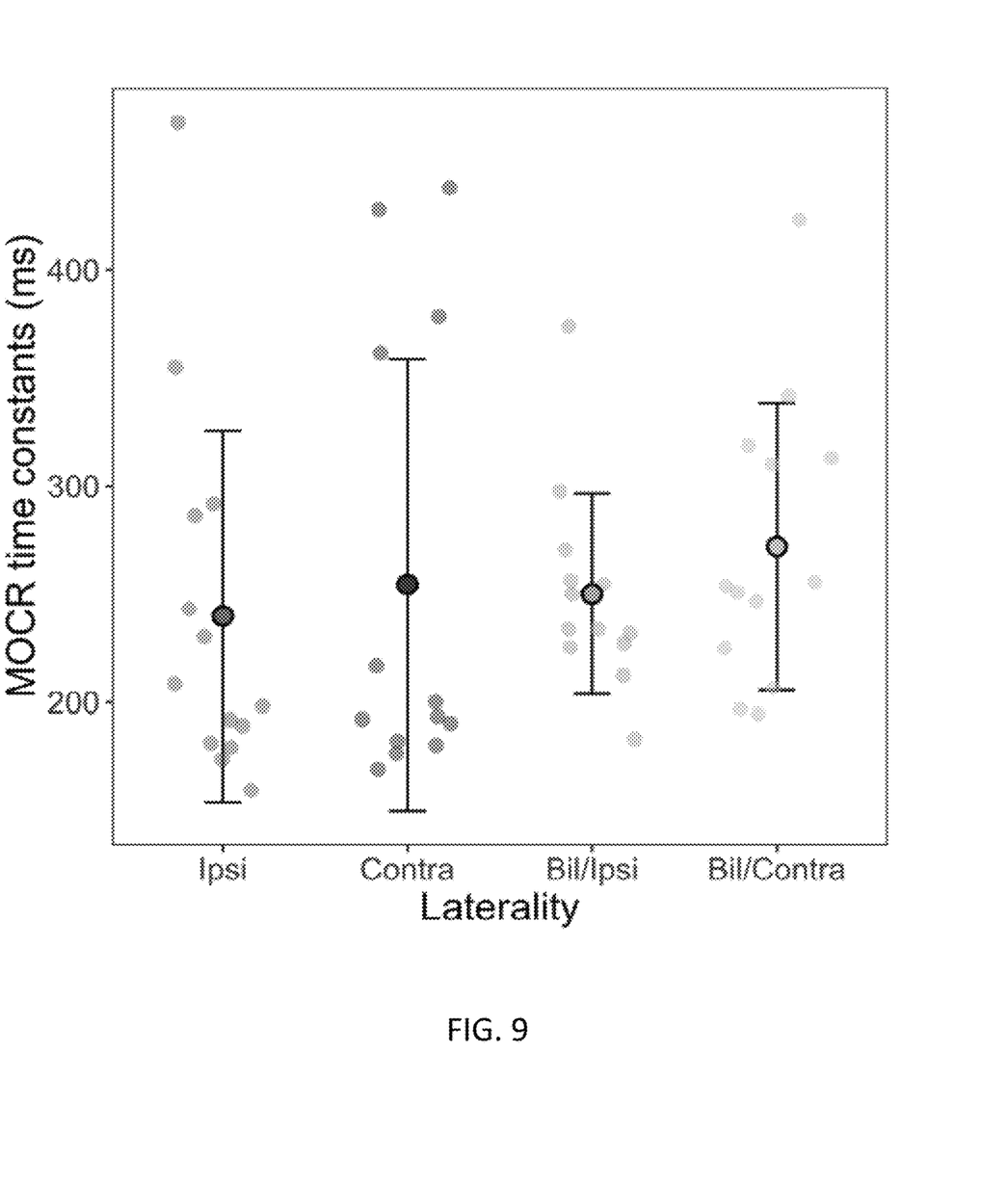
FIG. 9 illustrates MOCR time constants (τ) across laterality in the activator window according to aspects of the present disclosure.
Figure 10:
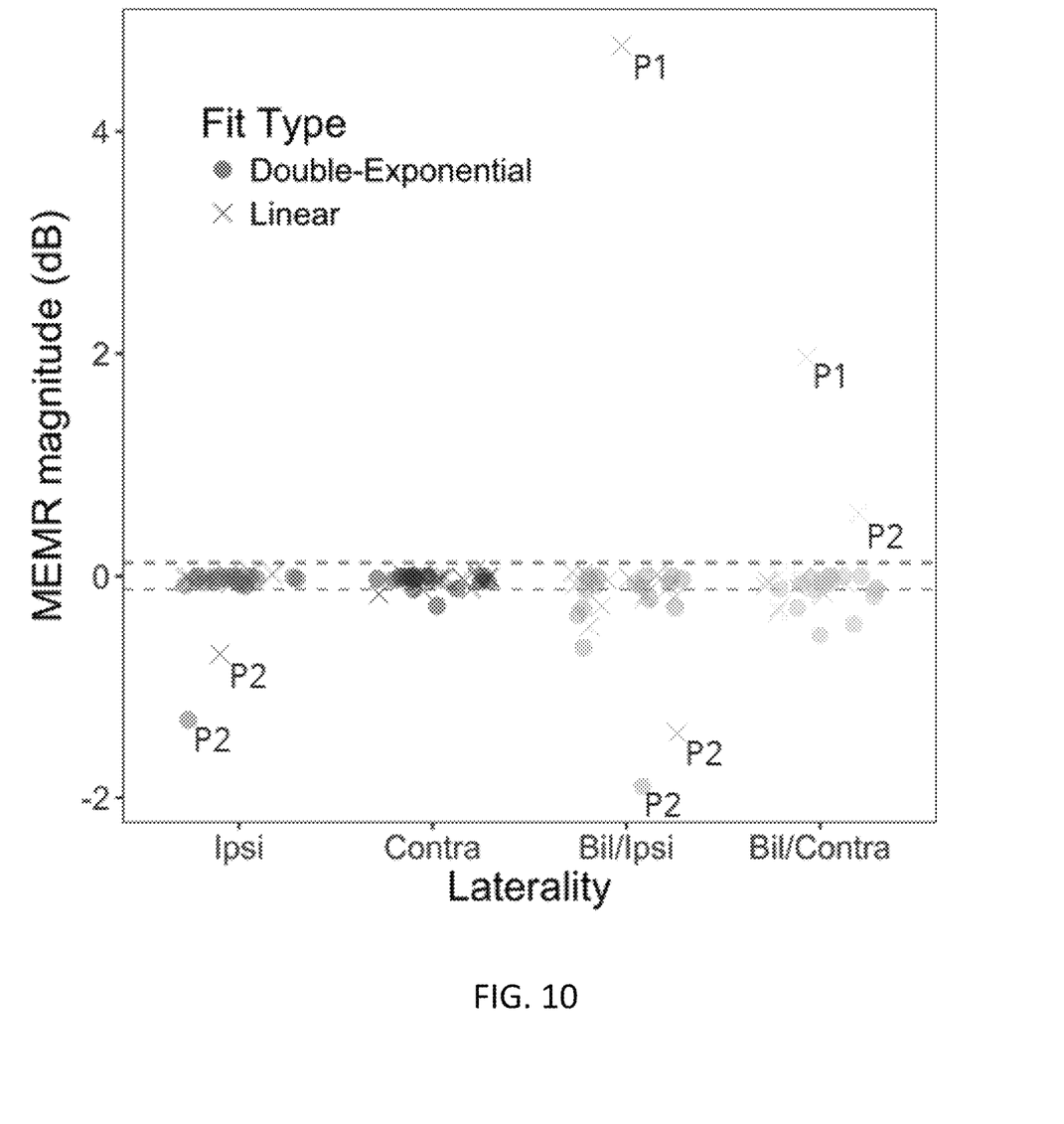
FIG. 10 is an illustration of estimates of MEMR magnitude showing the change in the stimulus level across time in comparison to a baseline obtained using either a double-exponential or linear fit according to aspects of the present disclosure.

Clicks are effective MOCR elicitors, particularly when used bilaterally. As shown in FIGS. 6 and 9, the change in CEOAE level across time and the resulting time constants are consistent with physiological and prior OAE reports. See Liberman et al. and Backus & Guinan. FIG. 6 shows the change in the CEOAE level (MOCR magnitude, $\Delta$dB) across time with respect to the baseline for click levels/rates for all 14 participants. Time-course resolution in the activation window is 32 ms. Both baselines show no change in CEOAE with advancing time but, CEOAEs in the activation and recovery windows reduce in amplitude and recover, respectively. Double-exponential lines were fit to the group mean data to extract mean CEOAE change ($\Delta$AB) and time constants ($\tau$). FIG. 9 shows MOCR time constants ($\tau$) across laterality in the activator window. The one-way ANOVA shows no significant effect of laterality (F[3,39]=0.7, p=0.6).

Outliers (rejected) are identified as P1 and P2. Dashed lines indicate the 0.12 dB limit considered as MEMR activation. FIG. 6 shows the change in the click stimulus level across time with respect to the baseline for click levels/rates for all 14 participants. Both baselines show no change in the click-stimulus with time. Clicks in the activation window reduce in amplitude. Clicks in the recovery window show large variability (possibly lower SNR). Double-exponential lines were fit to the group mean data. One-way ANOVA for the stimulus change in the activator data shows a significant effect of laterality ($F[1,16]=7$, $p=0.02$). Post-hocs (corrected for multiple comparisons) show bilateral activations producing larger MEMR effects with respect to both unilateral conditions. There was no difference between either unilateral or either bilateral condition.

The data suggest that the disclosed click-based method can be used to study cochlear, MOCR, and MEMR activity concurrently.

REFERENCES

Guinan, 2006. *Ear Hear,* 27(6), 589-607.
Winslow & Sachs, 1987. *J Neurophysiol,* 57(4), 1002-1021.
Maison & Liberman, 2000. *J Neurosci,* 20(12), 4701-4707.
Veuillet et al., 2007. *Brain,* 130(11), 2915-2928.
Wilson et al., 2017. *J Neurophysiol,* 118: 1164-1172, 2017.
Mertes & Goodman, 2016. *Ear Hear,* 37(2), e72-e84.
Mishra & Lutman, 2013. *Ear Hear,* 34(6), 789-798.
Abdala et al., 2014. *JASA,* 135(2), 754-765.
Liberman et al., 1996. *JASA,* 99(6), 3572-3584.
Backus & Guinan, 2006. *JASA,* 119(5), 2889-2904.
Boothalingam, S., Kurke, J. & Dhar, S., 2018. *JARO,* 19(4): 421-434.

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

What is claimed is:

1. A system operable to monitor and evaluate auditory efferent function of a patient comprising:
   a processing device,
      wherein the processing device is configured to generate and expose a patient to a window of short-duration acoustic activator click rate stimuli to generate a click-evoked otoacoustic emission (CEOAE) in each ear of the patient,
      wherein the processing device is configured to generate the short-duration click rate stimuli over a time-course, wherein the time course comprises a plurality of sub-windows, wherein the plurality of sub-windows comprises a baseline sub-window and an activation sub-window, and wherein the activation sub-window comprises short-duration acoustic activator click rate stimuli, and wherein a rate of activator click rate stimuli changes between the baseline sub-window and the activation sub-window,
      wherein the processing device is configured to concurrently sample an outer hair cell activity (OHC) and an efferent activity in each ear of the patient in response to exposing the patient to the activator click rate stimuli,
      wherein the processing device is configured to monitor a middle ear muscle reflex (MEMR) in each ear of the patient in response to exposing the patient to the click stimuli,
      wherein the processing device is configured to compare a CEOAE from the baseline sub-window to a CEOAE from the activation sub-window across the time-course to calculate a magnitude of CEOAE, and
      wherein the processing device is configured to measure a change on cochlear activity in the patient based on the CEOAE, the efferent activity, and the MEMR of each ear;
   a first probe and a second probe,
      wherein the first and the second probes are configured to transmit the activator click rate stimuli to each ear of the patient, and
      wherein the first and the second probes are configured to record the CEOAE, the efferent activity, and monitor the MEMR of each ear of the patient;
   a user interface; and
   a monitor.

2. The system of claim 1, wherein the processing device is further configured to communicate through one or more networks, wherein the one or more networks is an IP-based telecommunications network, the Internet, an intranet, a local area network, a wireless local network, a content distribution network, other types of communications network, or combinations of networks.

3. The system of claim 1, wherein the processing device is further configured to interface with a communication device.

4. The system of claim 3, wherein the communication device is a personal computer, a handheld computer, a mobile phone, a digital assistant, a smart phone, a server, an application, or combinations thereof.

5. The system of claim 3, wherein the communication device is configured to remotely interface with the first and second probes and/or the processing device when generating the activator click rate stimuli and recording the CEOAE, the efferent activity, and the MEMR of each ear of each ear of the patient.

6. The system of claim 1, wherein the processing device generates the activator click rate stimuli comprising a rate between 10 and 75 Hz.

7. The system of claim 1, wherein the processing device generates the activator click rate stimuli comprising a level between 50 and 90 dB peak-to-peak peak equivalent sound pressure level (ppeSPL).

8. The system of claim 1, wherein the processing device generates the short-duration click stimuli over a time-course, wherein the time-course is between 0.25 and 2 seconds.

9. A method of identifying an auditory disorder in a patient comprising evaluating an auditory efferent function of the patient with the system of claim 1.

10. The system of claim 1, wherein the wherein the plurality of sub-windows further comprises a first baseline sub-window, a second baseline sub-window, an activation sub-window, and a recovery sub-window.

11. The system of claim 10, wherein the processing device generates the activator click rate stimuli comprising a rate of 20 Hz in the first baseline sub-window, a rate of 10 Hz in the second baseline sub-window, a rate of 62.5 Hz in the activation sub-window, and 20 Hz in the recovery sub-window.

* * * * *